United States Patent [19]

Altschuler et al.

[11] 4,012,638
[45] Mar. 15, 1977

[54] DENTAL X-RAY ALIGNMENT SYSTEM

[76] Inventors: Bruce R. Altschuler, 123 Thornell, San Antonio, Tex. 78235; Vincent A. Segreto, 638 Candleglo Drive, San Antonio, Tex. 78239; Cecil E. Brown, Jr., 13203 Rhame Drive, Oxon-Hill, Md. 20022

[22] Filed: Mar. 9, 1976

[21] Appl. No.: 665,193

[52] U.S. Cl. .............................. 250/491; 250/338; 250/479
[51] Int. Cl.² ..................................... G01N 21/00
[58] Field of Search .......... 250/491, 338, 320, 323, 250/341, 460, 478, 479, 521

[56] References Cited

UNITED STATES PATENTS

| | | | |
|---|---|---|---|
| 2,090,933 | 8/1937 | Bolin | 250/521 |
| 2,553,028 | 5/1951 | Wright | 250/479 |
| 2,659,824 | 11/1953 | Burnham | 250/491 |
| 3,076,949 | 2/1963 | Anderson | 250/338 |
| 3,092,721 | 6/1963 | Medwedeff et al. | 250/491 |
| 3,777,160 | 12/1973 | Bernt | 250/338 |
| 3,861,807 | 1/1975 | Lescrenier | 250/491 |

*Primary Examiner*—Harold A. Dixon
*Attorney, Agent, or Firm*—Joseph E. Rusz

[57] ABSTRACT

Dental x-ray film is properly aligned with the x-ray beam utilizing a plurality of infrared emitters and detectors that are positioned circumferentially about the path of the x-ray beam. A reflecting surface whose plane is parallel with the plane of the x-ray film holder and integral therewith can be positioned parallel to the plurality of emitters and sensors by repositioning until the sensors receive a predetermined reflective response. Each sensor activates an indicator light seen on a display and when all the lights in a bank of lights are activated alignment is achieved. The output of the sensors can also be summed and when the sum output reaches a predetermined value an oscillator is triggered thus creating an audible tone indicating proper alignment.

5 Claims, 5 Drawing Figures

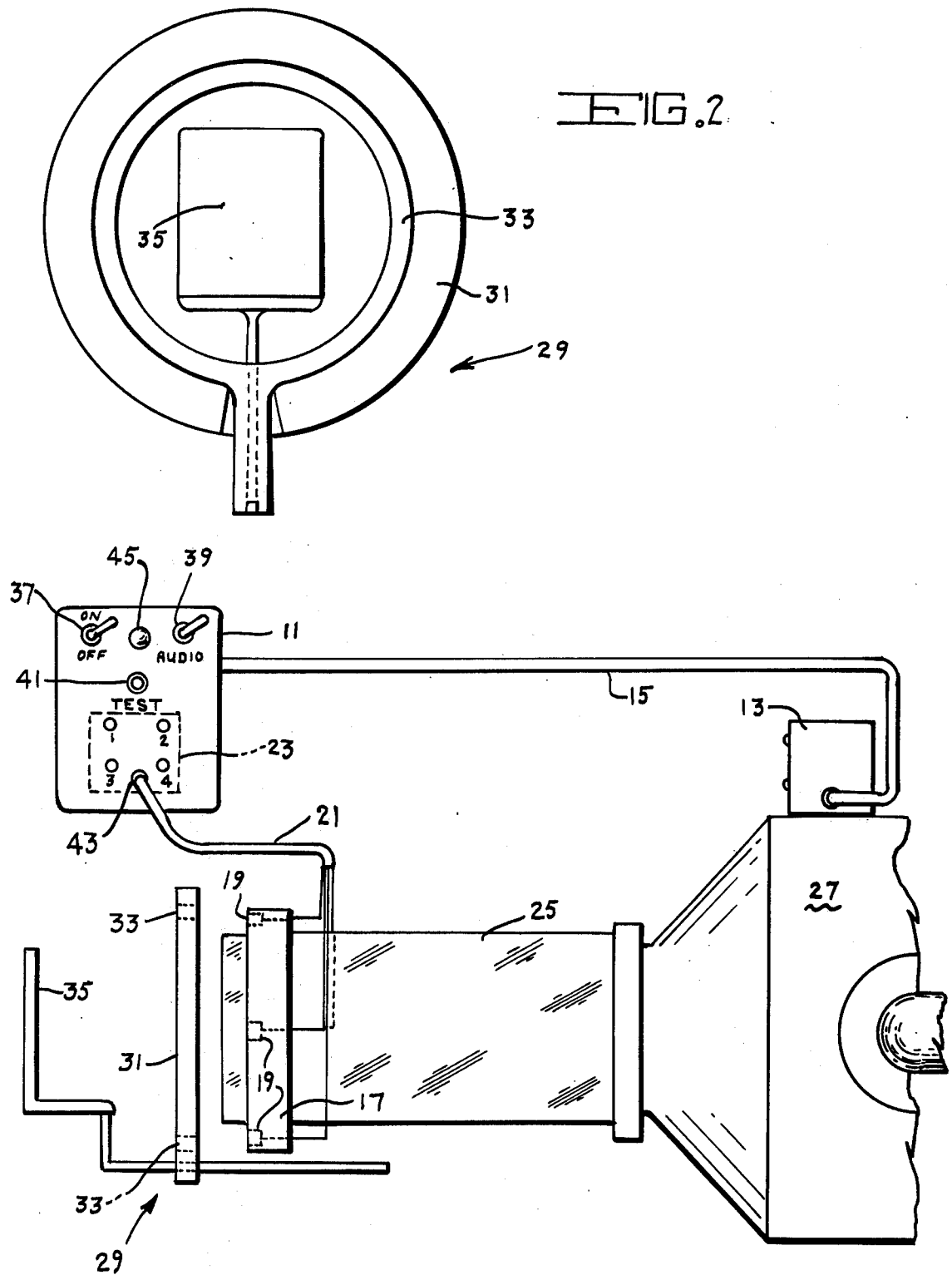

4,012,638

DENTAL X-RAY ALIGNMENT SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates to dental radiography, and more particularly to an electro-optic system for aligning dental x-ray film.

When a dentist or dental technician makes an x-ray of a patient's teeth there is the possibility that the x-ray film may not be in alignment with the x-ray beam, thus creating undesirable results.

The invention eliminates the problem of cone-cutting, misalignment due to operator error, misalignment due to patient movement, and misalignment due to tube-head "creep" shifting. The invention also solves problems related to repositioning of film during long-term studies (such as periodontal bone research). In addition, the invention provides an easy self-training method for dental assistant instruction.

SUMMARY OF THE INVENTION

The electro-optical radiographic alignment system of the present invention uses infrared electro-optical sensor to provide sight and sound feedback to a radiologist for precise alignment of dental films and holders with x-ray machines for optimum radiography. The system used infrared electro-optical emitters and sensors, to provide a variable signal which is coupled to light and tone indicators. The infrared emitters and detectors are arranged in pairs about the periphery of a ring or rectangle mount depending on the x-ray machine. The mount slips over and is attached to the output end of the x-ray source (usually the plastic cone, cylinder, or rectangle as the case may be. Each pair of emitter and detector is arranged or focused so that infrared light from the emitters when reflected from a plastic reflector attached to the periphery of a dental film holder will be of equal amplitude at the detector if the emitter/detector mount is aligned with the reflector.

It is therefore an object of this invention to provide a method and system of obtaining alignment of dental x-ray film with respect to the x-ray beam.

It is another object to provide a method and system of preventing dental x-ray misalignments due to operator error, patient movement, and two-head creep shifting.

It is still another object to provide a method and system of dental x-ray alignment which solves the repositioning of x-ray film during long-term studies.

These and other objects, features and advantages of the invention will become more apparent from the following detailed description when take in conjunction with the illustrative embodiment of the accompanying drawings.

DESCRIPTION OF THE DRAWINGS

FIG. 1 is a side elevation schematic view showing an embodiment of the invention.

FIG. 2 is a front elevation schematic view showing the film holder and the reflector assembly.

DETAILED DESCRIPTION OF THE PREFERRED EMBODIMENT

Figure 3:
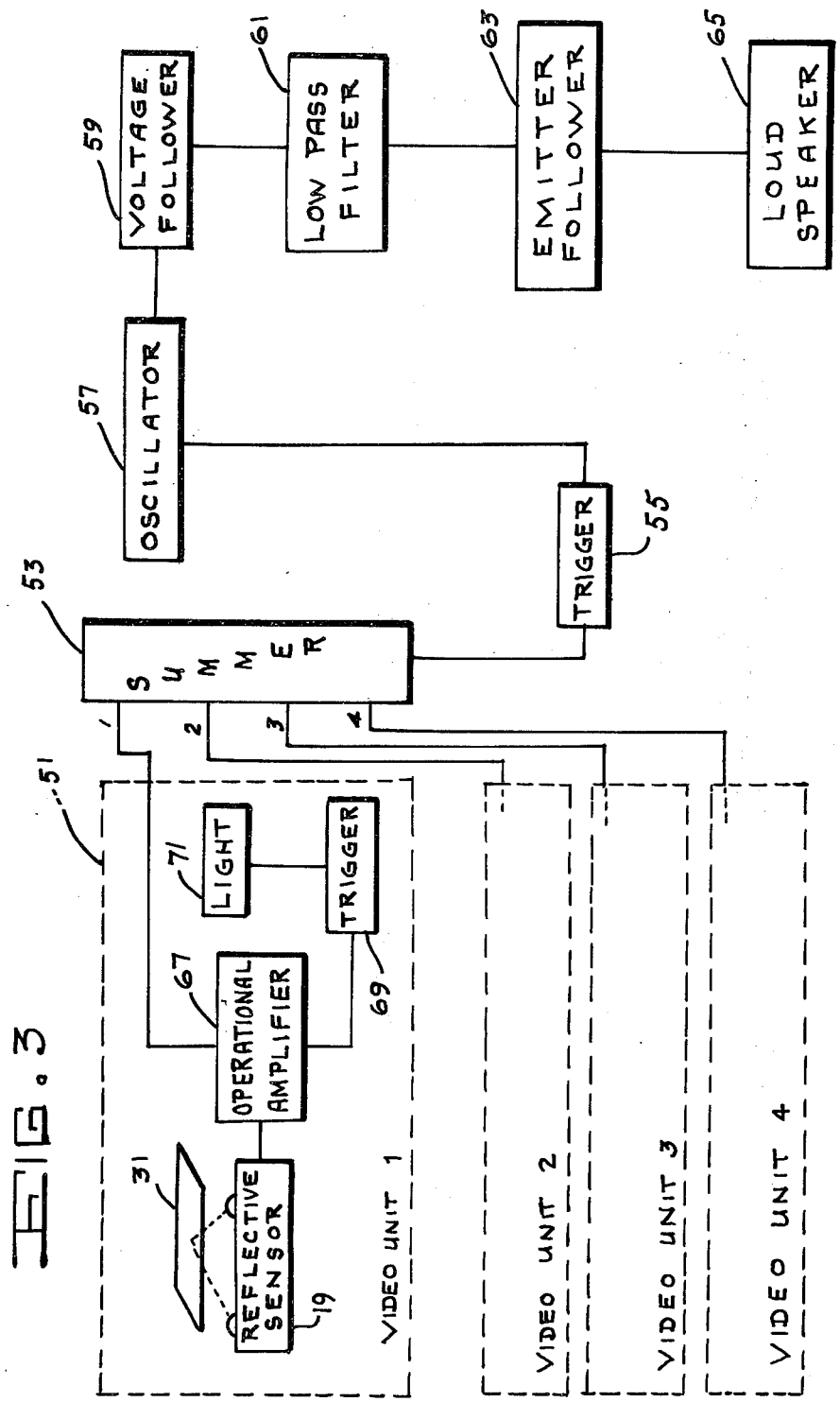
FIG. 3 is a block diagram showing an embodiment of the invention.

As shown in FIG. 1, the alignment system includes main control unit 11 and remote indicating unit 13 connected to main control unit 11 by cable 15. Ring assembly 17 or other appropriate shape has mounted therein a plurality of emitters and sensor pairs 19. In the present embodiment four such pairs are utilized which are connected to main unit 11 by cable 21. These pairs of emitters and sensors correspond to the indicator lights in light bank 23. Ring assembly 17 is attached to cylinder 25 (or a rectangular collimating cone) that connects to dental x-ray machine 27.

The reflecting assembly 29, also shown in FIG. 2, includes reflecting ring 31 which snaps on plastic aiming device 33 of intra-oral film holder 35 which can be of the XCP (extension cone parallel) type.

In ring mount assembly 17, emitters/sensors 19 can be infrared devices such as light emitting diodes (LEDs) and this assembly can fit onto plexiglas cylinder 25 of x-ray machine 27 by friction fit, glue, or small threaded screws.

Main control unit 11 as shown has three switches. Left switch 37 is the control while switch 39 connects the auido signal. Test button 41 allows a test of the lights to insure that they and their power supply are operable. The four lights of light bank 23 are seen at the bottom of control unit 11. A third switch, not visible, switches from the main control unit light bank 23 to the light bank of remote unit 13.

Remote unit 13 can be attached to a visible location on dental x-ray machine 27. As x-ray machine design varies by manufacturer, different sites for attachment may be used. Glue, tape, rubber bands, a metal clamp, rubber suction cups, or tapped screws may be used to attach the unit. Use of remote unit 13 is optional as the main central unit can provide alignment information; however, remote unit 13 may offer superior visibility in its location and can provide visual feedback to the patient in the anterior film position.

Ring mount assembly 17 is plugged into jack 43 on the front main control unit 11. The ring assembly is positioned on cylindrical cone 25 of x-ray machine 27. If a rectangular cone is used, then a suitable adapted rectangle alignment mount assembly should be used. Emitters/sensors 19 face the patient and cable 21 from the ring assembly 17 may be taped or otherwise retained to cylindrical cone 25 so as not to interfere with the patient.

In operation of the system, main control unit 11 is activated by plugging the outside power line into a standard grounded 115 volt single phase outlet. Switch 37 is placed in the ON position actuating amber light 45. Switch 39 may be placed in the ON position to activate the audio tone generator. The main/remote switch on the back of the unit (not shown) may be placed in either the main position to activate the main unit's light bank indicators 23 or to remote position to activate the light indicators of remote unit 13.

Test button 41 is depressed on main unit 11. All lights of the particular light bank indicated by the main/remote switch should go on. If the audio switch is in up position, a sound should be heard. Tone and loudness of the sound, and equalizing the brightness of the lights, may be controlled by trimmer screws (controlling potentiometers) inside the unit, if necessary.

Reflector ring 31 (or rectangle for rectangular cones) is snapped onto XCP plastic arming device 33. The XCP holder is used in the usual manner in the mouth, the film being positioned according to instructions for use with the XCP device. Other alignment film holders may be used with this invention, provided suitable ring mounts and reflector rings are adapted using the same principle.

For normal operation, the doctor chooses the proper XCP (or other instrument film) and exposure guidelines from experience for the proper exposure. As an example, in the case of a periapical radiograph of a central incisor, the anterior XCP film holder would be used. Reflector ring 31 is snapped onto anterior plastic aiming device 33. The XCP instrument for the periapical film is positioned in the normal manner. Cylinder 25 Cylinder 25 (tubehead cone) is positioned until edges are nearly parallel to reflector ring 31. The tone is heard and the lights on main unit 11 or on remote unit 13 are observed. The x-ray tubehead and cylinder are adjusted until all the four lights just come on with equal brightness and/or the tone is loudest. The patient may be instructed to observe the lights and position his/her head to illuminate the lights equally since feedback is immediate. When the unit is properly alighed, the x-ray exposure may be made in the usual manner; the unit should maintain its orientation when the operator removes his hands. If not, then the alignment should be readjusted and compensated for the slight "sway" in the x-ray machine. This invention will indicate creep or sway in the x-ray machine beyond tolerance levels indicates and when the x-ray tubehead requires repairs. Posterior and bitewing radiographs may be taken in a similar manner using posterior XCP film holders. The reflector ring will mount on both anterior and posterior plastic aiming devices.

In the above descriptions, the locations of the switches on the main control unit are for the particular prototype unit built. However, placement of switches can be placed anywhere for convenience of the operator.

A block diagram of the electrical system of the invention is shown in FIG. 3. In the presently described embodiment there are four similar video units, with video unit 51 being one of the four that are each fed to summer 53. Trigger 55 is activated by the output of summer 53 by a predetermined value and then trigger 55 activates oscillator 57. Following oscillator 57 is voltage follower 59, low pass filter 61, and emitter follower 63. Loudspeaker 65 is connected to emitter follower 63 thus causing an audible tone.

Video unit 51 includes reflector 31 and emitter/sensor 19 which is connected to operational amplifier 67. The output of operational amplifier 67 will cause trigger circuit 69 to activate light 71 upon reaching a predetermined value.

Figure 4:
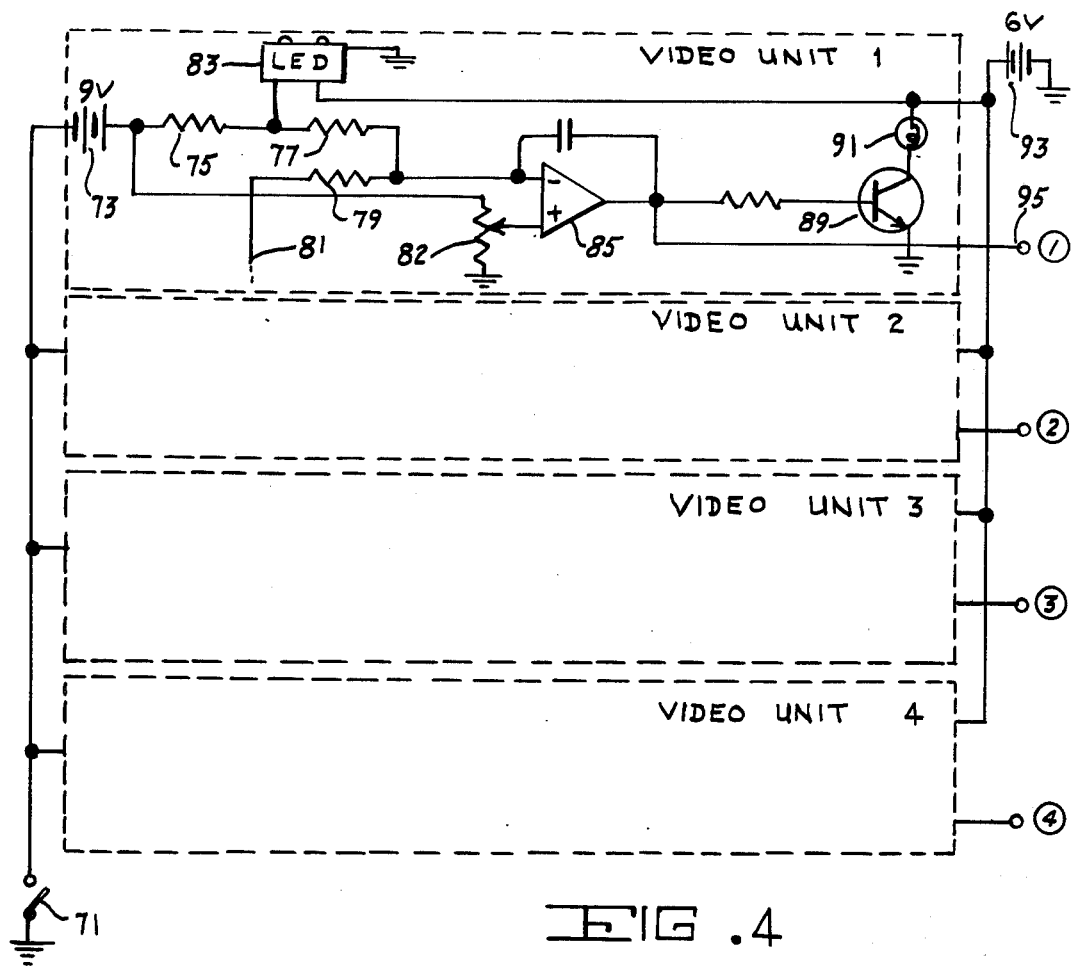
FIG. 4 is a detail of the video circuit shown in FIG. 3.

The circuits of FIG. 3 are shown in FIG. 4 which shows four video units one of which is presented and described in detail. Switch 71 controls the grounding of power supply 73 which connects to biasing resistors 75, 77, and 79. Lead 81 connects to the equivalent of resistor 79 and subsequent circuit elements in each of the other video units. Light emitting diode 83 is used as the source and sensor of infrared energy, however any other convenient source of infrared energy could be used and any appropriate source of radiant energy can be used instead of infrared energy. The negative terminal of operational amplifier 85 is resistively connected to the output of LED circuit 83 and the positive terminal is connected to potentiometer 87 used for adjustment of the quantity of sensed reflected radiation needed to trigger an indicator light. The base of transistor 89 is resistively coupled to operational amplifier 85 with its collector activating indicator light 91. Transistor 89 functions as a switch connecting six-volt power source 93 to ground, thus energizing light 91. The output of operational amplifier 85 is also connected to terminal 95, one of four feeding the summer that controls the audio output.

Figure 5:
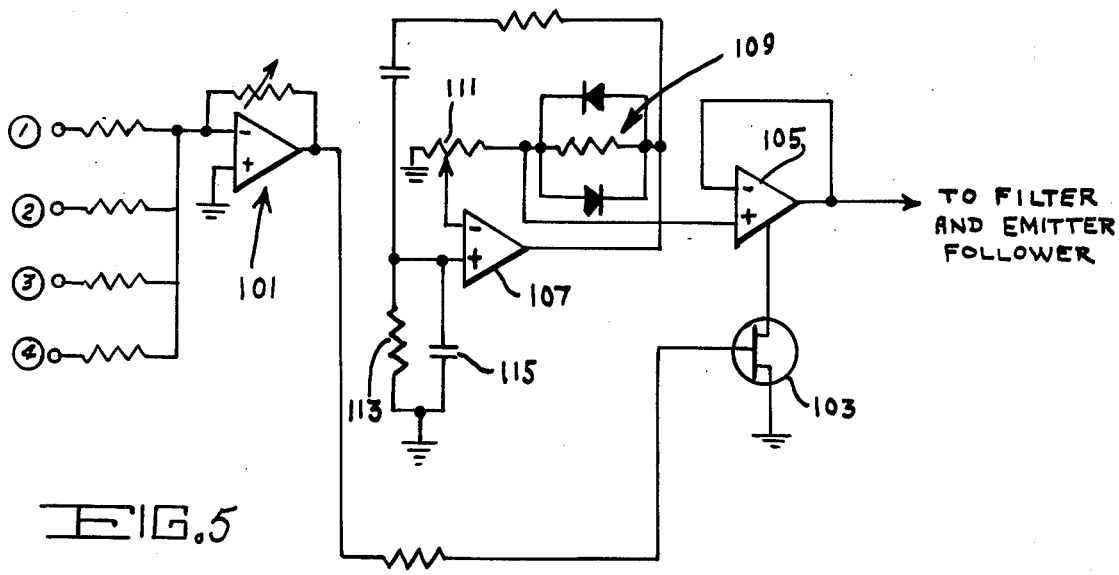
FIG. 5 is a detail of the summer, oscillator, trigger, and voltage follower circuits shown in FIG. 3.

The circuit of the audio system is shown in FIG. 5 in which the four outputs of the video unit are fed to operational amplifier 101 which functions as a summer. The gate of field effect transistor 103 is connected to operational amplifier 101 and activates operational amplifier 105. This amplifier is fed by operational amplifier 107 through protective diode circuit 109. The negative input of operational amplifier is connected to potentiometer 111 used for adjustment and the positive terminal is grounded through resistor 113 and capacitor 115.

What is claimed is:

1. An apparatus for the alignment of x-ray film with respect to an x-ray beam comprising:
    a. a plurality of pairs of radiators and sensors surrounding the path of the x-ray beam;
    b. a reflector positioned parallel to the x-ray film and integral therewith; and
    c. means for detecting if the plurality of sensors receive equal reflected radiation indicating the alignment of the x-ray film with the x-ray beam.

2. An apparatus for the alignment of x-ray film with an x-ray beam according to claim 1 wherein the detecting means include a display having a plurality of indicator lights with each indicator light triggered by one each of the plurality of sensors upon sensing a predetermined quantity of reflective radiation.

3. An apparatus for the alignment of x-ray film with respect to an x-ray beam according to claim 2 wherein the radiators emit infrared energy.

4. An apparatus for the alignment of x-ray film with an x-ray beam according to claim 3 which further comprises a plurality of operational amplifiers interposed between one each of the plurality of indicator lights and the plurality of sensors with each operational amplifier having potentiometer means for adjusting the predetermined quantity for triggering the indicator lights.

5. An apparatus for the alignment of x-ray film with an x-ray beam according to claim 1 wherein the detecting means comprise:
    a. a summer fed by the plurality of sensors;
    b. means for determining if the output of the summer has reached a predetermined value;
    c. an audio oscillator fed by said predetermined value determining means; and
    d. a loudspeaker connected to the audio oscillator.

* * * * *